United States Patent [19]

Chibata et al.

[11] 4,072,691

[45] Feb. 7, 1978

[54] PROCESS FOR THE RESOLUTION OF DL-6-CHLOROTRYPTOPHAN

[75] Inventors: Ichiro Chibata, Suita; Shigeki Yamada, Toyonaka; Masao Yamamoto, Hirakata; Hisato Sanematsu, Osaka, all of Japan

[73] Assignee: Tanabe Seiyaku Co., Ltd., Osaka, Japan

[21] Appl. No.: 681,426

[22] Filed: Apr. 29, 1976

Related U.S. Application Data

[63] Continuation of Ser. No. 538,107, Jan. 2, 1975, abandoned.

[30] Foreign Application Priority Data

Jan. 12, 1974 Japan .................................... 49-6779
July 9, 1974 Japan .................................... 49-78881
Aug. 2, 1974 Japan .................................... 49-89231

[51] Int. Cl.$^2$ ............................................ C07D 209/20
[52] U.S. Cl. ............................................ 260/326.14 T
[58] Field of Search ............................... 260/326.14 T

[56] References Cited

U.S. PATENT DOCUMENTS

| 2,813,876 | 11/1957 | Lyttle et al. | 260/326.14 T |
| 3,149,122 | 9/1964 | Sasaji et al. | 260/326.14 T |
| 3,825,559 | 7/1974 | Tazuke et al. | 260/326.14 T |
| 3,904,646 | 9/1975 | Chibata et al. | 260/326.14 T |

FOREIGN PATENT DOCUMENTS

1,269,851  4/1972  United Kingdom ........ 260/326.14 T

OTHER PUBLICATIONS

Shigeki et al., J. Agric. Food Chem. 23(4), 653–657 (1975).
Yamada et al., J. Org. Chem., vol. 38, No. 26, pp. 4408–4412 (1973).

*Primary Examiner*—Ethel G. Love
*Attorney, Agent, or Firm*—Bierman & Bierman

[57] ABSTRACT

Seed crystals of one optically active enantiomer of 6-chlorotryptophan methanesulfonate or 6-chlorotryptophan benzenesulfonate are added to a supersaturated solution of DL-6-chlorotryptophan methanesulfonate or DL-6-chlorotryptophan benzenesulfonate. Crystallization of the optically active enantiomer results. The crystals are recovered. Alternatively, crystals of the optically active enantiomer may be added to a hot solution of DL-6-chlorotryptophan methanesulfonate or DL-6-chlorotryptophan benzenesulfonate to produce a supersaturated solution. The solution is then cooled to crystallize out the optically active enantiomer. Optically active 6-chlorotryptophan is prepared by treating optically active 6-chlorotryptophan methanesulfonate or 6-chlorotryptophan benzenesulfonate with an alkaline agent or an ion exchange resin.

9 Claims, No Drawings

PROCESS FOR THE RESOLUTION OF DL-6-CHLOROTRYPTOPHAN

This application is a Continuation of parent application Ser. No. 538,107, filed on Jan. 2nd, 1975, now abandoned.

This invention relates to a process for the resolution of DL-6-chlorotryptophan. It also relates to a process for preparing optically active 6-chlorotryptophan.

D-6-chlorotryphtophan is useful as a nonnutritive sweetner. It is known that L-6-chlorotryptophan can be prepared by a fermentative method, i.e., by cultivating *Claviceps purpures* in a nutrient medium containing 6-chloroindole[Applied Microbiology, Vol.21, No.5, 841 – 843(1971)]. This method, however, is disadvantageous for the commercial production of L-6-chlorotryptophan due to its poor yield. On the other hand, synthetic 6-chlorotryptophan is optically inactive and consists of equal parts of the two enantiomorphic isomers. Hence, it follows that optical resolution is required to obtain optically active 6-chlorotryptophan. However, there is no report that DL-6-chlorotryptophan or a derivative thereof was resolved by the preferential crystallization method or the other methods.

Generally, a racemic modification of an organic compound can be resolved by preferential crystallization into each of its optically active enantiomers if the modification exists substantially in the form of the racemic mixture. However, it is impossible to predict whether a given racemic modification has such beneficial properties. It is likewise impossible to predict whether resolution of a given racemic modification is possible. Therefore, each pair of optically active enantiomers must be further studied experimentally to determine whether preferential crystallization can be accomplished. It is advantageous to commercially produce an optically active enantiomer by the preferential crystallization method. However, DL-6-chlorotryptophan itself cannot resolved by the preferential crystallization method.

As a result of various investigations, it has now been found that the salt of DL-6-chlorotryptophan with methanesulfonic acid or benzenesulfonic acid, that is, DL-6-chlorotryptophan methanesulfonate or DL-6chlorotryptophan benzenesulfonate, has many beneficial properties which enable one to preferentially crystallize it out into each of its optically active enantiomers. DL-6-chlorotryptophan methanesulfonate and DL-6-chlorotryptophan benzenesulfonate can be readily prepared in a conventional manner and a supersaturated solution of an enantiomer of these salts is stable even after the preferential crystallization of the other optically active enantiomer. Additionally, prompt crystallization of each of the enantiomers is afforded. Moreover, since DL-6-chlorotryptophan methanesulfonate and DL-6-chlorotryptophan benzenesulfonate have sufficiently higher solubility as compared with the corresponding enantiomers thereof, the desired optically active 6-chlorotryptophan methanesulfonate and 6-chlorotryptophan benzenesulfonate can be obtained in a high yield even when the preferential crystallization is carried out in an aqueous solution.

One object of the present invention is to provide a novel and useful process for resolving DL-6-chlorotryptophan. Another object of the invention is to provide a process for resolving DL-6-chlorotryptophan in a high yield and in a simple and convenient manner. Still another object of the invention is to provide an economical and commercially useful process for preparing optically active 6-chlorotryptophan. A further object of the invention is to provide novel intermediates which are useful in preparing optically active 6-chlorotryptophan. Still further objects of the invention will be apparent from the disclosure which follows.

According to the present invention, optically active 6-chlorotryptophan methanesulfonate and 6-chlorotryptophan benzenesulfonate can be prepared by the steps of producing a supersaturated solution of DL-6-chlorotryptophan methanesulfonate or DL-6-chlorotryptophan benzenesulfonate in a solvent; seeding or dissolving one of the optically active enantiomers thereof into the supersaturated solution thus making the predominant enantiomer to crystallize out preferentially; and then recovering it from the solution. 6-chlorotryptophan methanesulfonate and 6-chlorotryptophan benzenesulfonate, in the form of either the racemic modification or optically active enantiomer, are novel compounds which can be readily prepared. For example, DL-6-chlorotryptophan methanesulfonate and DL-6-chlorotryptophan benzenesulfonate can be prepared by neutralilizing DL-6-chlorotryptophan with methanesulfonic acid or benzenesulfonic acid in a suitable solvent. Optically active 6-chlorotryptophan methanesulfonate and 6-chlorotryptophan benzenesulfonate are also prepared in the same manner as above.

The supersaturated solution of the racemic modification can be prepared by applying conventional procedures, such as, for example, refrigeration, concentration, addition of an appropriate solvent or a combination of these operations, to a solution of DL-6-chlorotryptophan methanesulfonate or DL-6-chlorotryptophan benzenesulfonate. However, it is most convenient to prepare by cooling a hot solution saturated with DL-6-chlorotryptophan methanesulfonate or DL-6-chlorotryptophan benzenesulfonate, because the solubility thereof increases as the temperature becomes higher. Additionally, DL-6-chlorotryptophan methanesulfonate and DL-6-chlorotryptophan benzenesulfonate which are employed in preparing the supersaturated solution may not be always an equal mixture of D- and L-enantiomers. It is convenient to use an unequal mixture thereof as the starting material of the present invention, because the predominant enantiomer in the mixture may, upon cooling, be spontaneously crystallized out from the supersaturated solution of said material.

When the supersaturated solution of the racemic modification is prepared as above, a small amount of crystals of one of the enantiomers is seeded to the supersaturated solution as a seed, and the mixture is stirred. Preferential crystallization of the enantiomer which is the same as that seeded results. Alternatively, a small amount of one of the enantiomers is dissolved in a hot solution of the racemic modification in order to make said enantiomer predominant over the other enantiomer in the solution. The solution is then cooled, whereby spontaneous crystallization of the predominant enantiomer takes place. It is also possible to combine these procedures. That is, a part of the crystals of one of the enantiomers is dissolved in the solution of the racemic modification and the remaining part of the seed crystals is used to be seeded into the supersaturated solution in which one of the enantiomers is dominant over the other. In this case, the amount of seed added can be minimized. The seed crystals employed in the present invention should have a high optical purity. The greater the amount of the seed, the better the resultant resolution. However, the practical proportion to the seed to be added is generally within the range of about 0.005 to 5% based on the weight of the solution. Although the temperature at which the preferential crystallization is carried out is not critical for the invention, a temperature of 10° to 50° C is preferred. The crystallization is enhanced by stirring the solution. Any inert solvent in which DL-6-chlorotryptophan methanesulfonate or DL-6-chlorotryptophan benzenesulfonate can be dissolved and which can afford prompt crystallization of the compound is suitable for the process of preferential crystallization. Examples of inert solvents, suitable for this process, are water, a mixture of water and an alkanol having one to 6 carbon atoms, and a mixture of water and an alkanone having 3 to 6 carbon atoms. However, water is the most suitable solvent from an industrial standpoint.

The mother liquor which is obtained after isolation of oneof the enantiomers by the above-mentioned procedure can be again employed for the optical resolution of the other enantiomer. For example, when a certain amount of the racemic modification which is equal to the amount of the enantiomer previously separated is added to the mother liquor, the same conditions as the previous operation can be obtained except that the predominant enantiomer in the solution will be the antipode of the enntiomer previously separated. Thus, the operation of preferential crystallization can be repeated indefinitely, and the racemic modification which is supplied can be successively and entirely resolved into each of the D- and L-enantiomeres.

The process of the present invention can be carried out batchwise, as mentioned above, or in a continuous manner. A continuous process, for example, would comprise passing the supersaturated solution through a column containing the seed crystals, and allowing an optically active 6-chlorotryptophan methanesulfonate or 6-chlorotryptophan benzenesulfonate to crystallize out in the column. Alternatively, the process of the present invention can be carried out by immersing the seeding plates of optically active enantiomers in the supersaturated solution and allowing the optically active enantiomers to crystallize out on the seeding plates.

Depending upon the degree of supersaturation and the amount of crystallization, the crystals of the optically active enantiomers thus obtained may sometimes be optically impure. The crude crystals, however, can be easily purified because the solubility of the racemic modification is sufficiently higher than that of each enantiomer and the one optically active enantiomer can not remain dissolved in the saturated solution of the racemic modification. For example, optically pure crystals of 6-chlorotryptophan methanesulfonate and 6-chlorotryptophan benzenesulfonate can be obtained by adding the crude crystals to sufficient solvent to produce a solution saturated or almost saturated with respect to the racemic modification in the crude crystals, stirring the solution, and recovering the resultant crystals from the solution. Alternatively, the optically pure crystals of 6-chlorotryptophan methanesulfonate and 6-chlorotryptophan benzenesulfonate can be obtained by dissolving the crude crystals at an elevated temperature in a small amount of a solvent which will dissolve the racemic modification in the crude crystals, saturating or almost saturating the solution with respect to the racemic modification to crystallize the enantiomer, and recovering the crystallized enantiomer from the solution. Such operations as refrigeration, concentration, addition of a solvent or combination thereof may be used for saturating or almost saturating the solution. The same solvent as described above can also be employed for this purpose. In order to promote crystallization of the optically active enantiomer, crystals of the optically active enantiomer may be seeded into the solution saturated or almost saturated with the racemic modification. In case that only a small amount of solvent is needed due to low contents of the racemic modification in the crude crystals or the high solubility of the racemic modification, it is convenient to carry out the operation by adding suitable amount of a solution saturated with the racemic modification.

According to the present invention, the optically active enantiomer thus obtained can be readily converted into optically active 6-chlorotryptophan. Optically active 6-chlorotryptophan is prepared by treating optically active 6-chlorotryptophan methanesulfonate or 6-chlorotryptophan benzenesulfonate with an alkaline agent such as an inorganic base(e.g., sodium hydroxide, potassium hydroxide, lithium hydroxide, ammonium hydroxide), an organic base(e.g., methylamine, ethylamine, cyclohexylamine)or with an ion exchange resin (e.g., Amberlite IR-120, Dowex 50W) to remove methanesulfonic acid or benzenesulfonic acid therefrom. The thus obtained methanesulfonic acid and benzenesulfonic acid can be re-used for preparing the starting materials of the invention, i.e., DL-6-chlorotryptophan methanesulfonate and DL-6-chlorotryptophan benzenesulfonate. Practical and presently-preferred embodiments of the present invention are shown in the following.

EXAMPLE 1

119.4 g of DL-6-chlorotryptophan and 50.9 g of methanesulfonic acid are dissolved in 1000 ml of water under heating. The mixture is treated with activated carbon. The filtrate is concentrated to a volume of about 400 ml and allowed to stand in a refrigerator overnight. The crystalline precipitate thus formed is collected by filtration, washed with cold water and then dried under reduced pressure. 94.9 g of DL-6-chlorotryptophan methanesulfonate are obtained as the initial crop. M.p. 234° – 236° C(decomp.) Furthermore, 64.1 g of DL-6-chlorotryptophan methanesulfonate are obtained by successive concentration of the combined filtrate. Total amount: 159.0 g. The product is used for resolution without further purification. Slow crystallization of the product from water gives a racemic mixture showing the following physico-chemical properties.

M.p. 237° – 238° C(decomp.)
$[\alpha]_{436}^{25} = 0°(c=0.5, N-HCl)$
Solubility in water(g/100 ml) at 25° C: 73.5
Analysis calculated for $C_{12}H_{15}O_5N_2ClS$: C, 43.05; H, 4.52; N, 8.37; Cl, 10.59; S, 9.58; Found: C, 43.14; H, 4.55; N, 8.39; Cl, 10.72; S, 9.73

L-6-chlorotryptophan methanesulfonate and D-6-chlorotryptophan methanesulfonate are prepared in the same manner as described above.

L-6-chlorotryptophan methanesulfonate:
M.p. 256° – 257° C(decomp.)
$[\alpha]_{436}^{25} = +25.6°(c=0.5, N-HCl)$
Solubility in water(g/100 ml) at 25° C: 30.8
Analysis calculated for $C_{12}H_{15}O_5ClS$: C, 43.05; H, 4.52; N, 8.37; Cl, 10.59; S, 9.58
Found: C, 43.22; H, 4.60; N, 8.41; Cl, 10.52; S, 9.53
D-6-chlorotryptophan methanesulfonate:

M.p. 256° –0 257° C(decomp.)
[α]$_{436}^{25}$ = − 25.6°(c=0.5, N-HCl)
Solubility in water(g/100 ml) at 25° C: 30.8

EXAMPLE 2

119.4 g of DL-6-chlorotryptophan and 98.2 g of benzenesulfonic acid are dissolved in 2300 ml of water under heating. The mixture is treated with activated carbon. The filtrate is concentrated to a volume of about 500 ml, and then allowed to stand in a refrigerator overnight. The crystalline precipitate is collected by filtration, washed with cold water and then dried under reduced pressure. 198.0 g of DL-6-chlorotryptophan benzenesulfonate are obtained.

M.p. 237° – 239° C(decomp.)
Solubility in water(g/100 ml) at 25° C: 1.8
L-6-chlorotryptophan benzenesulfonate and D-6-chlorotryptophan benzenesulfonate are prepared in the same manner as described above.

L-6-chlorotryptophan benzenesulfonate:
 M.p. 247° – 249° C(decomp.)
 [α]$_D^{25}$ = + 7.0°(c=1.0, N-HCl)
 [α]$_{436}^{25}$ = + 18.1°(c=1.0, N-HCl)
 Solubility in water(g/100 ml) at 25° C: 0.82

D-6-chlorotryptophan benzenesulfonate:
 M.p. 247° – 249° C(decomp.)
 [α]$_D^{25}$ = − 7.0°(c=1.0, N-HCl)
 [α]$_{436}^{25}$ = − 18.1°(c=1.0, N-HCl)
 Solubility in water(g/100 ml) at 25° C: 0.82

EXAMPLE 3

(1) 94.0 g of DL-6-chlorotryptophan methanesulfonate are dissolved in 100 ml of water under heating. The solution is cooled to 25° C, and 3.0 g of L-6-chlorotryptophan methanesulfonate are seeded into the solution. The solution is stirred at 25° C for 45 minutes. The crystalline precipitate thus formed is collected by filtration, washed with 5 ml of cold water, and then dried. 8.8 g of L-6-chlorotryptophan methanesulfonate are obtained.

[α]$_{436}^{25}$ = + 24.5°(c=0.5, N-HCl)
Optical purity: 96%

(2) 8.0 g of L-6-chlorotryptophan methanesulfonate obtained in (1) are dissolved in 40 ml of water under heating. The solution is adjusted to pH 6.0 with a 5N-ammonium hydroxide aqueous solution, and then allowed to stand in a refrigerator overnight. The crystalline precipitate thus formed is collected by filtration, washed with cold water, and then dried. 5.4 g of L-6-chlorotryptophan are obtained.

[α]$_D^{25}$ = + 10.3°(c=1.0, N-HCl)
Physico-chemical properties of the product recrystallized from 50%(v/v) methanol are:
[α]$_D^{25}$ = + 10.7°(c=1.0, N-HCl)
M.p. 264° – 265° C(decomp.)

EXAMPLE 4

(1) 47.0 g of DL-6-chlorotryptophan methanesulfonate and 3.0 g of D-6-chlorotryptophan methanesulfonate are dissolved in 50 ml of water under heating. The solution is cooled to 25° C, and 50 mg of D-6-chlorotrypthophan methanesulfonate are seeded into the solution. The solution is stirred at 25° C for 80 minutes. The crystalline precipitate thus formed is collected by filtration, washed with 2.5 ml of cold water, and then dried. 5.9 g of D-6-chlorotryptophan methanesulfonate are obtained.

8 α]$_{436}^{25}$ = − 23.7°(c=0.5, N-HCl)
Optical purity: 93%

(2) 5.0 g of D-6-chlorotryptophan methanesulfonate obtained in (1) are dissolved in 25 ml of water under heating. The solution is adjusted to pH 6.0 with a 5N-ammonium hydroxide aqueous solution, and then allowed to stand in a refrigerator overnight. The crystalline precipitate thus formed is collected by filtration, washed with cold water, and then dried. 3.6 g of D-6-chlorotryptophan are obtained.

[α]$_D^{25}$ = − 10.0°(c=1.0, N-HCl)

(3) 6.0 g of DL-6-chlorotryptophan methanesulfonate are dissolved in the mother liquor obtained in (1) under heating. The solution is cooled to 25° C, and 50 mg of L-6-chlorotryptophan methanesulfonate are seeded into the solution. The solution is stirred at 25° C for 80 minutes. The crystalline precipitate thus formed is collected by filtration, washed with 2.5 ml of cold water, and then dried. 5.8 g of L-6-chlorotryptophan methanesulfonate are obtained.

[α]$_{436}^{25}$ = + 24.0°(c=0.5, N-HCl)

EXAMPLE 5

(1) 8.90 g of L-6-chlorotryptophan methanesulfonate (Optical purity: 85.0%) are dissolved, under heating, in a mixture of 1.90 ml of water and 20.0 ml of an aqueous solution saturated at 25° C with DL-6-chlorotryptophan methanesulfonate. The solution is cooled to 25° C, and 2 mg of L-6-chlorotryptophan methanesulfonate are seeded into the solution. The solution is mildly stirred for 7.5 hours. The crystalline precipitate thus formed is collected by filtration, washed with 3 ml of cold water, and then dried. 7.49 g of L-6-chlorotryptophan methanesulfonate are obtained.

[α]$_{436}^{25}$ = + 25.4°(c=1.0, N-HCl)
Optical purity: 99.0%

(2) 7.00 g of L-6-chlorotryptophan methanesulfonate obtained in (1) are dissolved in 35.0 ml of water under heating. The solution is adjusted to pH 6.0 with a 5N-ammonium hydroxide aqueous solution, and then allowed to stand in a refrigerator overnight. The crystalline precipitate thus formed is collected by filtration, washed with cold water, and then dried. 4.74 g of L-6-chlorotryptophan are obtained.

[α]$_D^{25}$ = + 11.0°(c=1.0, N-HCl)

(3) The mother liquor obtained after the isolation of L-6-chlorotryptophan methanesulfonate is treated with activated carbon and then concentrated. The crystalline precipitate thus formed is collected by filtration, washed with cold water, and then dried. 9.50 g of DL-6-chlorotryptophan methanesulfonate are obtained.

[α]$_{436}^{25}$ = 0.0°(c=1.0, N-HCl)

(4) 7.0 g of DL-6-chlorotryptophan methanesulfonate obtained in (3) are dissolved in 35.0 ml of water under heating. The solution is adjusted to pH 6.0 with a 5N-ammonium hydroxide aqueous solution, and then allowed to stand in a refrigerator overnight. The crystalline precipitate thus formed is collected by filtration, washed with cold water, and then dried. 4.80 g of DL-6-chlorotryptophan are obtained.

EXAMPLE 6

(1) 9.50 g of D-6-chlorotryptophan methanesulfonate (Optical purity: 24.0 %) are dissolved in 9.90 ml of water under heating. The solution is cooled to 25° C, and 2 mg of D-6-chlorotryptophan methanesulfonate are seeded into the solution. The solution is mildly stirred for 7.5 hours. The crystalline precipitate thus formed is collected by filtration, washed with one ml of cold water, and then dried. 2.27 g of D-6-chlorotophan methanesulfonate are obtained.

$[\alpha]_{436}^{25} = -25.4°(c=1.0, \text{N-HCl})$

Optical purity: 99.0%

(2) 2.00 g of D-6-chlorotryptophan methanesulfonate obtained in (1) are dissolved in 100 ml of water under heating. The solution is adjusted to pH 6.0 with a 5N-ammonium hydroxide aqueous solution, and then allowed to stand in a refrigerator overnight. The crystalline precipitate thus formed is collected by filtration, washed with cold water, and then dried. 1.38 g of D-6-chlorotryptophan are obtained.

$[\alpha]_D^{25} = -10.4°(c=1.0, \text{N-HCl})$ (3) The mother liquor obtained after the isolation of D-6-chlorotryptophan methanesulfonate is treated with activated carbon and then concentrated. The crystalline precipitate thus formed is collected by filtration, washed with cold water, and then dried. 6.93 g of DL-6-chlorotryptophan methanesulfonate are obtained.

$[\alpha]_{436}^{25} = 0.0°(c=1.0, \text{N-HCl})$ (4) 6.00 g of DL-6-chlorotryptophan methanesulfonate obtained in (3) are treated in the same manner as described in Example 5-(4). 3.46 g of DL-6-chlorotryptophan are obtained.

EXAMPLE 7

(1) 16.3 g of DL-6-chlorotryptophan benzenesulfonate are dissolved in 250 ml of water under heating. The solution is cooled to 25° C, and 0.1 g of L-6-chlorotryptophan benzenesulfonate is seeded into the solution. The solution is stirred at 25° C for 60 minutes. The crystalline precipitate thus formed is collected by filtration, washed with one ml of cold water, and then dried. 1.2 g of L-6-chlorotryptophan benzenesulfonate are obtained.

$[\alpha]_{436}^{25} = +15.4°(c=1.0, \text{methanol})$ Optical purity: 85.0%

(2) 1.0 g of L-6-chlorotryptophan benzenesulfonate obtained in (1) is dissolved in 11 ml of water under heating. The solution is adjusted to pH 6.0 with a 4N-sodium hydroxide aqueous solution, and then allowed to stand in a refrigerator overnight. The crystalline precipitate thus formed is collected by filtration, washed with 0.5 ml of cold water, and then dried. 0.55 g of L-6-chlorotryptophan is obtained.

$[\alpha]_D^{25} = +9.4°(c=1.0, \text{N-HCl})$

EXAMPLE 8

(1) 15.5 g of DL-6-chlorotryptophan benzenesulfonate and 1.0 g of D-6-chlorotryptophan benzenesulfonate are dissolved in 250 ml of water under heating. The solution is cooled to 25° C, and 0.1 g of D-6-chlorotryptophan benzenesulfonate is seeded into the solution. The solution is stirred at 25° C for 70 minutes. The crystalline precipitate thus formed is collected by filtration, washed with one ml of cold water, and then dried. 2.5 g of D-6-chlorotryptophan benzenesulfonate are obtained.

$[\alpha]_{436}^{25} = -16.5°(c=1.0, \text{N-HCl})$

Optical purity: 91.0%

(2) 2.3 g of D-6-chlorotryptophan benzenesulfonate obtained in (1) are dissolved in 26 ml of water under heating. The solution is adjusted to pH 6.0 with a 4N-sodium hydroxide aqueous solution, and then allowed to stand in a refrigerator overnight. The crystalline precipitate is collected by filtration, washed with cold water, and then dried. 1.3 g of D-6-chlorotryptophan are obtained.

$[\alpha]_D^{25} = -10.0°(c=1.0, \text{N-HCl})$ (3) 2.8 g of DL-6-chlorotryptophan benzenesulfonate are dissolved in the mother liquor obtained in (1) under heating. The solution is cooled to 25° C, and 0.1 g of L-6-chlorotryptophan benzenesulfonate is seeded into the solution. The solution is stirred at 25° C for 70 minutes. The crystalline precipitate is collected by filtration, washed with one ml of cold water, and then dried. 2.4 g of L-6-chlorotryptophan benzenesulfonate are obtained.

$[\alpha]_{436}^{25} = +16.7°(c=1.0, \text{N-HCl})$

Optical purity: 92.0%

(4) 2.2 g of L-6-chlorotryptophan benzenesulfonate are treated in the same manner as described in Example 7-(2). 1.2 g of L-6-chlorotryptophan are obtained.

$[\alpha]_D^{25} = +10.1°(c=1.0, \text{N-HCl})$

EXAMPLE 9

(1) 3.00 g of L-6-chlorotryptophan benzenesulfonate (Optical purity: 85%) are added to 26.0 ml of water. The mixture is stirred at 25° C overnight. The crystalline precipitate thus formed is collected by filtration, washed with one ml of cold water, and then dried. 2.50 g of L-6-chlorotryptophan benzenesulfonate are obtained.

$[\alpha]_{436}^{25} = +17.7°(c=1.0, \text{N-HCl})$

Optical purity: 98.0%

(2) 2.20 g of L-6-chlorotryptophan benzenesulfonate obtained in (1) are dissolved in 24.2 ml of water under heating. The solution is adjusted to pH 6.0 with a 4N-sodium hydroxide aqueous solution, and then allowed to stand in a refrigerator overnight. The crystalline precipitate thus formed is collected by filtration, washed with cold water, and then dried. 1.30 g of L-6-chlorotryptophan are obtained.

$[\alpha]_D^{25} = +10.3°(c=1.0, \text{N-HCl})$ (3) The mother liquor obtained after the isolation of L-6-chlorotryptophan benzenesulfonate is treated with activated carbon and then concentrated. The crystalline precipitate thus formed is collected by filtration, washed with cold water, and then dried. 0.40 g of DL-6-chlorotryptophan benzenesulfonate is obtained.

(4) 0.40 g of DL-6-chlorotryptophan benzenesulfonate obtained in (3) is dissolved in 6.0 ml of water under heating. The solution is adjusted to pH 6.0 with a 4N-sodium hydroxide aqueous solution, and then allowed to stand in a refrigerator overnight. The crystalline precipitate thus formed is collected by filtration, washed with cold water, and then dried. 0.22 g of DL-6-chlorotryptophan is obtained.

$[\alpha]_D^{25} = 0.0°(c=1.0, \text{N-HCl})$

EXAMPLE 10

(1) 3.30 g of D-6-chlorotryptophan benzenesulfonate (Optical purity: 91.0%) are added to 17.2 ml of water. The mixture is stirred at 25° C overnight. The crystalline precipitate thus formed is collected by filtration, washed with cold water, and then dried. 2.90 g of D-6-chlorotryptophan benzenesulfonate are obtained.

$[\alpha]_{436}^{25} = -17.7°(c=1.0, \text{N-HCl})$

Optical purity: 98.0%

(2) 2.50 g of D-6-chlorotryptophan benzenesulfonate obtained in (1) are dissolved in 40.0 ml of water under heating. The solution is adjusted to pH 6.0 with a 4N-sodium hydroxide aqueous solution, and then allowed to stand in a refrigerator overnight. The crystalline precipitate thus formed is collected by filtration, washed with cold water, and then dried. 1.44 g of D-6-chlorotryptophan are obtained.

$[\alpha]_D^{25} = -10.2°(c=1.0, \text{N-HCl})$ (3) The mother liquor obtained after the isolation of D-6-chlorotryptophan benzenesulfonate is treated with activated carbon and then concentrated. The crystalline precipitate thus formed is collected by filtration, washed with cold water, and then dried. 0.29 g of DL-6-chlorotryptophan benzenesulfonate is obtained.

$[\alpha]_{436}^{25} = 0.0°(c=1.0, \text{N-HCl})$ (4) 0.15 g of DL-6-chlorotryptophan benzenesulfonate obtained in (3) is treated in the same manner as described in Example 9-(4). 0.08 g of DL-6-chlorotryptophan is obtained.

What we claim is:

1. A process for resolving DL-6-chlorotryptophan methanesulfonate into its optically active enantiomers, which comprises the steps of adding a first enantiomer to a solution of DL-6-chlorotryptophan methanesulfonate, whereby a first supersaturated solution with respect to DL-6-chlorotryptophan methanesulfonate is formed, to initiate crystallization of said first enantiomer from said first supersaturated solution, and recovering the crystallized first enantiomer.

2. The process of claim 1 wherein said first enantiomer is added as seed crystals to said first supersaturated solution.

3. The process of claim 1 wherein said first enantiomer is added to said solution at an elevated temperature, then said solution is cooled to produce said first supersaturated solution.

4. The process of claim 3 further comprising innoculating said first supersaturated solution with seed crystals of said first enantiomer.

5. The process of claim 1 wherein said solution contains an inert solvent selected from the group consisting of water, a mixture of water and an alkanol having one to 6 carbon atoms, or a mixture of water and an alkanone having 3 to 6 carbon atoms.

6. The process of claim 1 further comprising the steps of dissolving, at an elevated temperature, additional DL-6-chlorotryptophan methanesulfonate in a mother liquor obtained after the recovery of said crystallized first enantiomer, cooling said mother liquor to form a second supersaturated solution, adding crystals of a second enantiomer to said second supersaturated solution to initiate crystallization of said second enantiomer from said second supersaturated solution, and recovering said second crystallized enantiomer.

7. The process of claim 1 wherein said process is repeated a plurality of times, whereby said first and second enantiomers are successively and alternatively separated as crystals from said solution.

8. The process of claim 7 further comprising the steps of dissolving the crystals of said first recovered enantiomer in a solvent to form a second solution whereby DL-6-chlorotryptophan methanesulfonate present in said crystals is dissolved, saturating or almost saturating said second solution with respect to DL-6-chlorotryptophan methanesulfonate to crystallize said first enantiomer from said second solution, and recovering the crystallized first enantiomer.

9. A process for preparing optically active 6-chlorotryptophan which comprises the steps of supersaturating an aqueous solution of DL-6-chlorotryptophan methanesulfonate, adding crystals of a first optically active enantiomer of 6-chlorotryptophan methanesulfonate to said supersaturated solution, crystallizing said first optically active enantiomer from said supersaturated solution, recovering said first crystallized optically active enantiomer, and then treating said recovered first optically active enantiomer with an alkaline agent or an ion-exchange resin.

* * * * *